United States Patent
Tepic et al.

(10) Patent No.: US 9,549,809 B2
(45) Date of Patent: Jan. 24, 2017

(54) ACL PROSTHESIS AND ANCHOR THEREFOR

(75) Inventors: Slobodan Tepic, Zurich (CH); Randall Acker, Ketchum, ID (US)

(73) Assignee: Kyon AG, Zurich (CH)

( * ) Notice: Subject to any disclaimer, the term of this patent is extended or adjusted under 35 U.S.C. 154(b) by 255 days.

(21) Appl. No.: 12/107,070

(22) Filed: Apr. 21, 2008

(65) Prior Publication Data
US 2011/0319994 A1 Dec. 29, 2011

Related U.S. Application Data

(60) Provisional application No. 60/913,275, filed on Apr. 21, 2007.

(51) Int. Cl.
*A61F 2/08* (2006.01)
*A61L 27/50* (2006.01)
(Continued)

(52) U.S. Cl.
CPC .............. *A61F 2/08* (2013.01); *A61F 2/0811* (2013.01); *A61L 27/50* (2013.01); *A61F 2002/0829* (2013.01); *A61F 2002/0841* (2013.01); *A61F 2002/0864* (2013.01); *A61F 2002/0882* (2013.01); *A61F 2002/0888* (2013.01); *A61F 2210/0004* (2013.01); *A61F 2220/0008* (2013.01); *A61F 2230/0004* (2013.01); *A61F 2230/0006* (2013.01);
(Continued)

(58) Field of Classification Search
CPC .............. A61F 2/08; A61F 2002/0817; A61F 2002/0823; A61F 2002/0829; A61F 2002/0835; A61F 2002/0841; A61F 2002/0847; A61F 2002/0852; A61F 2002/0858; A61F 2002/0864; A61F 2002/087;A61F 2002/0876; A61F 2002/0882; A61F 2002/0888; A61F 2/0811; A61B 17/06166; A61B 2017/06171; A61B 17/0401; A61B 2017/0458
USPC .............. 623/13.11–13.2; 606/232, 300–321
See application file for complete search history.

(56) References Cited

U.S. PATENT DOCUMENTS 3,540,452 A * 11/1970 Langner et al. ............... 606/231
3,762,418 A * 10/1973 Wasson ......................... 606/226
(Continued)

FOREIGN PATENT DOCUMENTS

WO    WO 9210149 A1 * 6/1992 ............... A61F 2/08

OTHER PUBLICATIONS

Azom. "Polyethylene Terephthalate Polyester ( PET, PETP )—Properties and Applications—Supplier Data by Goodfellow". Downloaded from <http://www.azom.com/article.aspx?ArticleID=2047> on Apr. 19, 2012.*

*Primary Examiner* — Andrew Iwamaye
(74) *Attorney, Agent, or Firm* — Occhiuti & Rohlicek LLP (57) ABSTRACT

An interarticular ligament prosthesis is formed from a plurality of high strength high modulus polymeric fibers. The fibers are independent and free from intrinsic inter-fiber shear coupling found in braided or bonded fibers. The ligament prosthesis is installed with tubular, bone screw anchors. The fibers of the ligament prosthesis pass through the central hole of the anchors and are knotted at one end. The exit holes of the anchors include ceramic eyelets with polished edges. The edges are rounded to a defined radius for desired fatigue life of the prosthesis.

18 Claims, 6 Drawing Sheets

(51) Int. Cl.
*A61L 27/36* (2006.01)
*A61L 27/52* (2006.01)

(52) U.S. Cl.
CPC ............... *A61F 2230/0069* (2013.01); *A61F 2250/0019* (2013.01); *A61F 2250/0021* (2013.01); *A61F 2250/0031* (2013.01); *A61F 2250/0032* (2013.01); *A61F 2250/0039* (2013.01); *A61F 2250/0041* (2013.01); *A61L 27/36* (2013.01); *A61L 27/3645* (2013.01); *A61L 27/52* (2013.01); *A61L 2300/104* (2013.01); *A61L 2430/10* (2013.01); *A61L 2430/24* (2013.01); *A61L 2430/34* (2013.01)

(56) References Cited

U.S. PATENT DOCUMENTS

| | | | |
|---|---|---|---|
| 4,149,277 A * | 4/1979 | Bokros | 623/13.2 |
| 4,642,119 A * | 2/1987 | Shah | 623/13.2 |
| 4,773,910 A * | 9/1988 | Chen et al. | 623/13.2 |
| 5,176,708 A * | 1/1993 | Frey et al. | 623/13.2 |
| 5,197,983 A * | 3/1993 | Berman et al. | 623/13.2 |
| 5,268,001 A * | 12/1993 | Nicholson et al. | 606/232 |
| 5,456,722 A * | 10/1995 | McLeod et al. | 128/898 |
| 5,545,180 A * | 8/1996 | Le et al. | 606/232 |
| 5,571,139 A * | 11/1996 | Jenkins, Jr. | 606/232 |
| 5,575,819 A * | 11/1996 | Amis | 623/13.13 |
| 5,843,574 A * | 12/1998 | Suryadevara et al. | 428/364 |
| 6,517,542 B1 * | 2/2003 | Papay et al. | 606/232 |
| 6,599,289 B1 * | 7/2003 | Bojarski et al. | 606/60 |
| 6,663,630 B2 * | 12/2003 | Farley et al. | 606/54 |
| 7,883,528 B2 * | 2/2011 | Grafton et al. | 606/232 |
| 2003/0065361 A1 * | 4/2003 | Dreyfuss | 606/232 |
| 2004/0193217 A1 * | 9/2004 | Lubbers et al. | 606/232 |
| 2004/0224406 A1 * | 11/2004 | Altman et al. | 435/395 |
| 2004/0267362 A1 * | 12/2004 | Hwang et al. | 623/13.15 |
| 2005/0203622 A1 * | 9/2005 | Steiner et al. | 623/13.14 |
| 2005/0222619 A1 * | 10/2005 | Dreyfuss et al. | 606/232 |
| 2006/0100630 A1 * | 5/2006 | West, Jr. | 606/73 |
| 2006/0276841 A1 * | 12/2006 | Barbieri et al. | 606/232 |
| 2008/0051888 A1 * | 2/2008 | Ratcliffe et al. | 623/13.18 |

* cited by examiner

FIGURE 1

PRIOR ART

FIGURE 2

PRIOR ART

ACL PROSTHESIS AND ANCHOR THEREFOR

CROSS-REFERENCES TO RELATED APPLICATIONS

This application claims priority to U.S. Provisional patent application Ser. No. 60/913,275, filed Apr. 21, 2007.

BACKGROUND OF THE INVENTION

1. Field of the Invention

The invention relates to an Anterior Cruciate Ligament (ACL) prosthesis and an anchor to fix its ends into bones. More particularly, it relates to an ACL prosthesis formed of a plurality of independent filaments and an anchor for minimizing wear and failure.

2. Discussion of Related Art

Anterior Cruciate Ligament (ACL) in the human knee joint, commonly called Cranial Cruciate Ligament in the canine stifle, is frequently torn in trauma, or, as it happens in dogs, fails after a degenerative process of still unknown etiology. Direct repair is usually not possible—when attempted, it predictably fails.

In human orthopedics, the standard procedure calls for replacement by an allograft, a part of the patellar ligament, or a part of the tendon removed from hamstring muscles. The procedure results in a stable knee, but the long term performance is often unsatisfactory with over a half of cases resulting in arthrosis of the joint.

In dogs the standard procedure is either an extracapsular suture (usually placed on the lateral side of the joint) approximating the function of the ligament, or one of the geometry modifying surgical techniques, e.g. Tibial Plateau Leveling Osteotomy (TPLO), Cranial Closing Wedge Osteotomy (CWO), or Tibial Tuberosity Advancement (TTA). Intra-articular prostheses are also occasionally used, but those generally end up in failure. Extracapsular sutures also fail. These are intended to provide stability of the joint for several weeks while waiting for fibrosis to form around the joint, which then should provide for long term stability. Arthrosis of the joint at longer term, at a year or so, is the rule rather exception.

Figure 1:
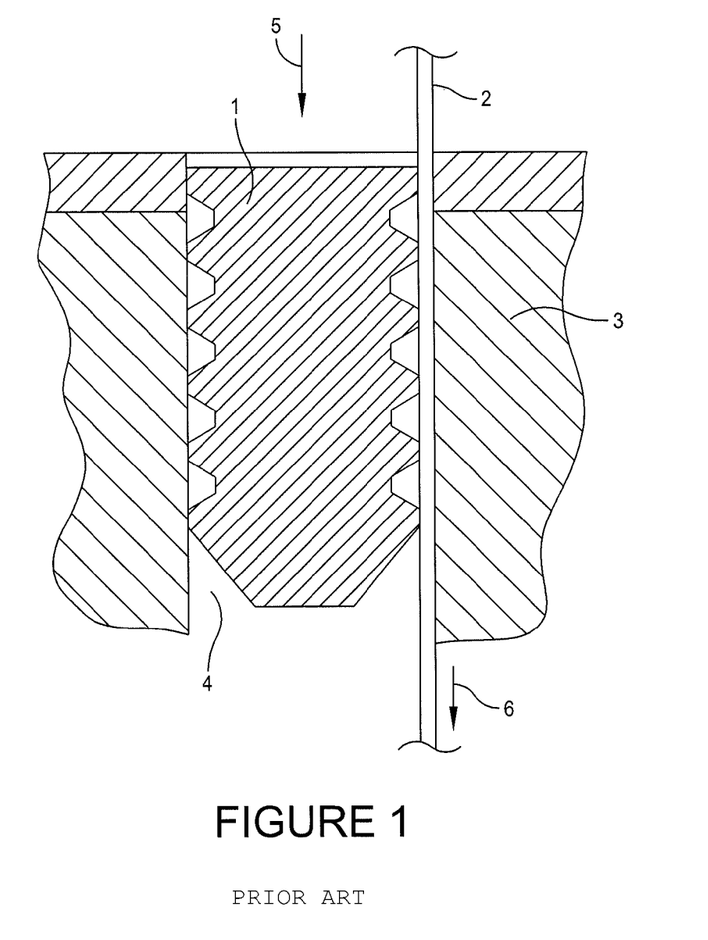
FIG. 1 is a cross sectional view of a state of the art interference screw for anchoring a ligament replacement tissue within a bone tunnel.

There are a variety of anchors used to fix the ends of an ACL prosthesis into bones. Most commonly, they are so-called interference screws, designed to be inserted along the prosthesis (transplanted tendon or ligament, or an artificial ligament) within an anchor hole, or tunnel, drilled in the bone. The interference screw jams the prosthetic tissue against the bone within the anchor hole. FIG. 1 shows an ACL bone anchor 1 of the interference screw type inserted into bone 3 in the direction 5 so as to jam the prosthetic tissue 2 within the hole 4 which can then resist pull-out force 6. Such screws are made either from metal, most commonly titanium, or bioresorbable polymers.

Figure 2:
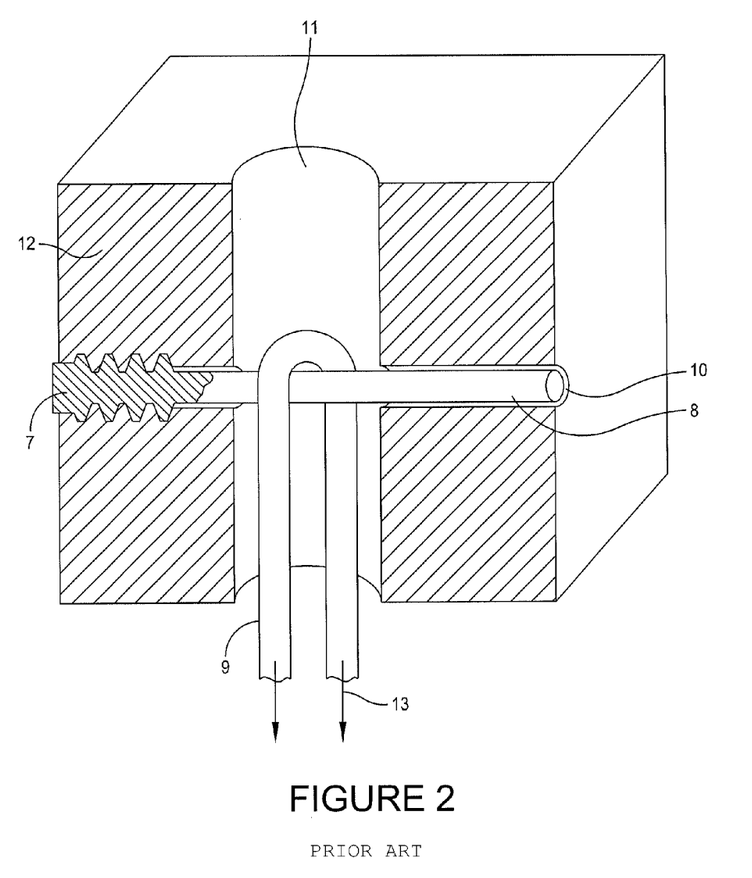
FIG. 2 is a cross sectional view of a state of the art transverse pin for anchoring ACL replacement in the lateral condyle of the femur.

Another common technique is so-called cross-pin used to anchor a loop of the prosthetic tissue within a hole drilled in the femoral condyle. In all cases, prosthetic tissue exits the tunnel by bending over the edge of the bone; healing/remodeling of the bone is expected to fill the gaps and to result in a natural-like anchorage of the ligament in the bone. FIG. 2 shows an ACL anchor 7 of the transverse, or cross pin type, inserted into the bone of the femoral condyle 12 through a hole 10. A front section 8 of the anchor 7 passes through a loop of prosthetic tissue 9 inserted through hole 11. In this manner the prosthetic tissue can support the pull 13.

Neither of these techniques is suitable for a permanent anchorage of an artificial ACL replacement. Bending of the prosthesis over the edge of the hole will lead to both, bone loss due to contact resorption and mechanical damage—ultimately failure—of the prosthesis due to bending and wear at the edge of the hole.

An alternative method of using screw anchors with the prosthesis fixed in their central, axial hole also do not provide for a durable anchorage, because in all known designs the bending of the prosthesis over the edge of the hole exceeds the fatigue limit of even the best materials used for prosthesis.

SUMMARY OF THE INVENTION

The present invention substantially overcomes the problems of existing ACL prostheses by providing a prosthesis made from high performance polymeric fibers. According to one aspect of the invention, the ACL prosthesis is formed of a plurality of independent filaments or fibers. Such fibers may include oriented, high modulus, ultra high molecular weight polyethylene available from either DSM, Netherlands as DYNEEMA, or from Honeywell, USA as SPECTRA. The invention further includes anchors for use with the ACL prosthesis. The anchors are tubular so that the ACL prosthesis can be threaded through the anchor and fixed within the bone. According to one aspect of the invention, the anchor has a radius at the edge of the exit hole to prevent wear of the ACL prosthesis. According to one aspect of the invention, the radius at the edge of the exit hole from the anchor exceeds a given ratio to the fiber diameter. According to another aspect of the invention, the ratio has an order of magnitude of about 100. According to another aspect of the invention, the fibers of the ACL prosthesis have a diameter on the order of 10 micrometers and the radius is on the order of 1 mm.

According to another aspect of the invention the anchors are made from titanium, or a titanium alloy. According to another aspect of the invention, the anchors include a separate eyelet at an exit hole. The eyelet is made from a ceramic providing a smooth, hard surface for the radius. According to another aspect of the invention, the eyelet is of ruby or sapphire.

DETAILED DESCRIPTION

The present invention includes a novel ACL prosthesis and an anchor therefor. The ACL prosthesis is formed of a plurality of independent filaments. Individual filaments have small diameters in order to limit the bending strain. Multiple filaments operate together to provide the necessary strength for the ACL prosthesis. The filaments are not braided or bonded in order to increase the bending strength. A novel anchor attaches the ACL prosthesis to the bone.

Figure 3A:
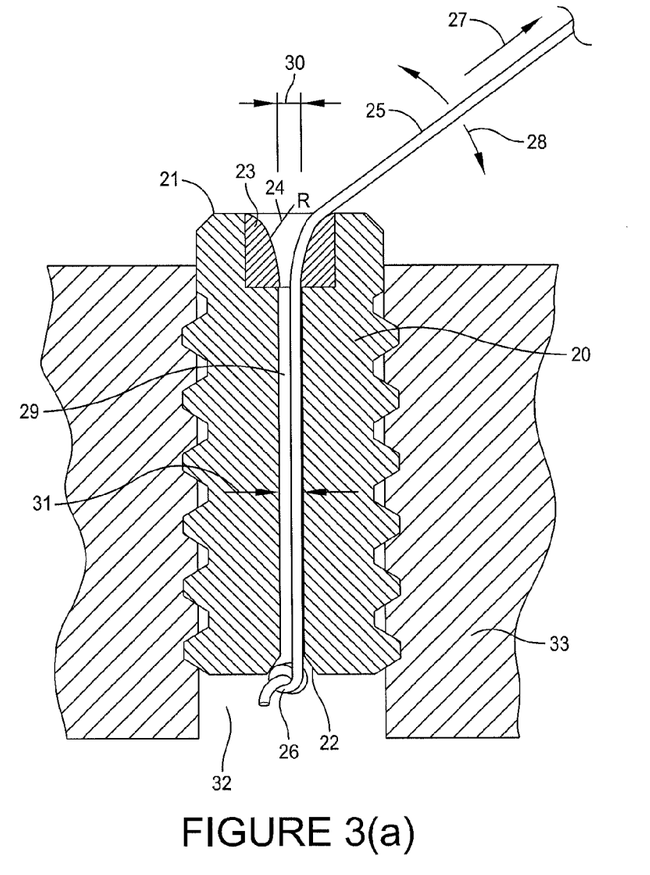
FIG. 3(a) is a cross sectional view of an ACL anchor in the bone according to an embodiment of the present invention.

FIG. 3(a) shows a cross sectional view of the bone anchor 21 according to an embodiment of the invention inserted into bone 33. The body 20 of the anchor is threaded, the threads being preferably self-tapping. A hole 29 is drilled through the whole anchor. At the tip of the anchor, the hole 29 is conical 22, and has a well-rounded edge. The head 34 of the anchor has a recess for accepting a ring or eyelet 23. The eyelet 23 has a central hole of diameter 30, which is smaller than the diameter 31 of the hole 29. The eyelet entry edge is rounded with radius 24. Prosthesis 25 passes through the hole in the eyelet and the hole 29 in the anchor body. At the tip of the anchor a knot 26 prevents pull-out under tension 27 on the prosthesis 25. The prosthesis 25 may swing through an angle 28 from the end of the anchor 21.

Figure 3B:
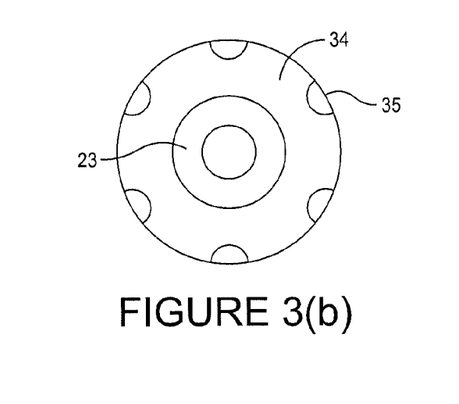
FIG. 3(b) is a top view of an ACL anchor according to an embodiment of the present invention.

FIG. 3(b) is a top view of the anchor 21. A set of grooves 35 are formed in the head 34 of the anchor 21. To install the anchor, a hole 32 is drilled in the bone 33. A special screwdriver engages the grooves 35 in order to rotate the anchor 21 to drive it into the hole 32.

Figure 4A:
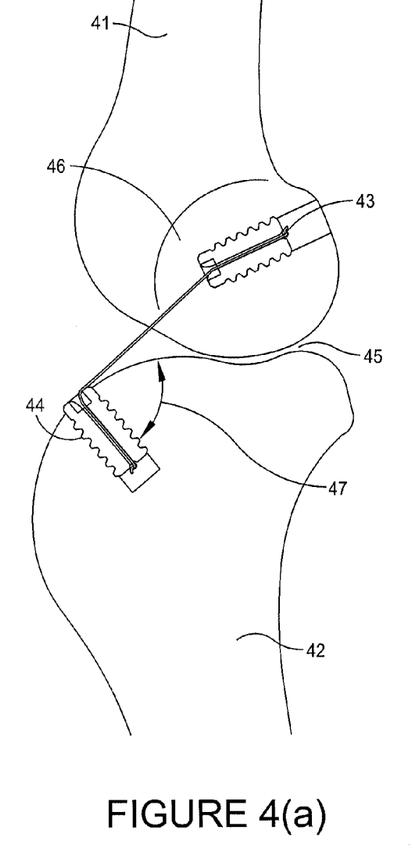
FIGS. 4(a)-4(d) are views of an ACL prosthesis according to an embodiment of the present invention in the knee.
Figure 4B:
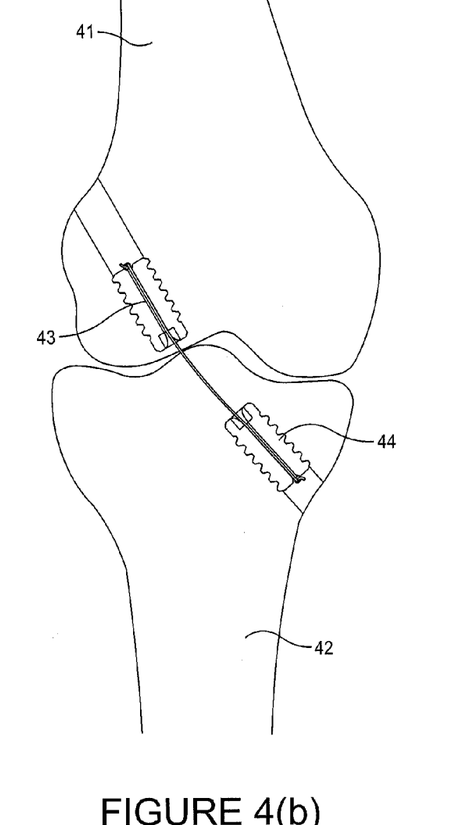
Figure 4C:
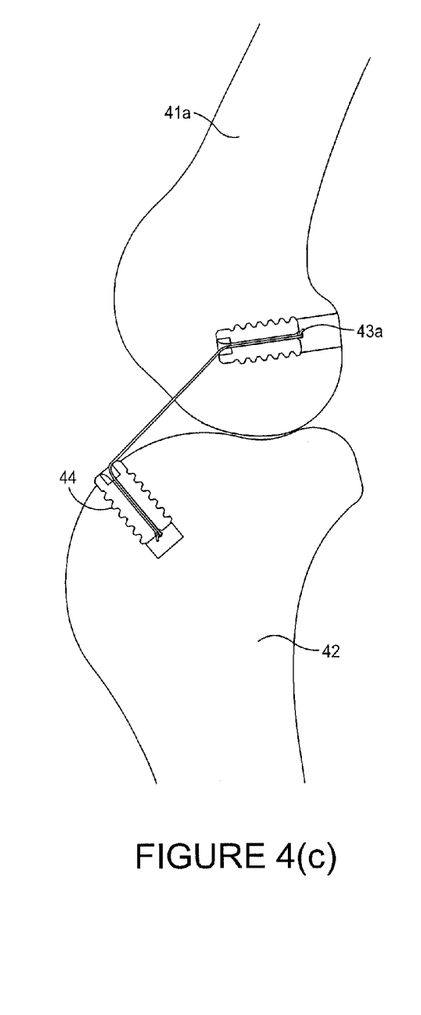
Figure 4D:
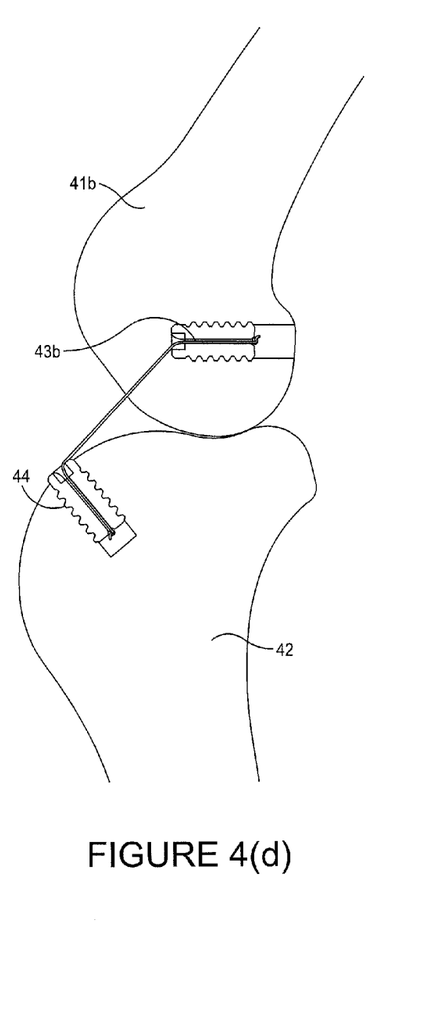

FIGS. 4(a) and 4(b) show lateral and frontal views, respectively, of the knee joint with the prosthetic ligament 45 according to an embodiment of the invention fixed to the tibia 42 with the anchor 44 and to the femur 41 with the anchor 43. With the movement of the joint, shown in FIGS. 4(c) and 4(d), the later being in full flexion, the angle 47 between the anchor 44 and the ligament 45, and the angle 46 between the anchor 43 and the ligament 45 change, implying flexion of the ligament over the edge of the anchor. It is also clear, but not shown in the frontal view that the ligament will undergo some rotational movement at the exit of the anchor. The prosthesis and anchor of the present invention minimize the strain and wear on the ligament from flexion and rotational movement.

Figure 5A:
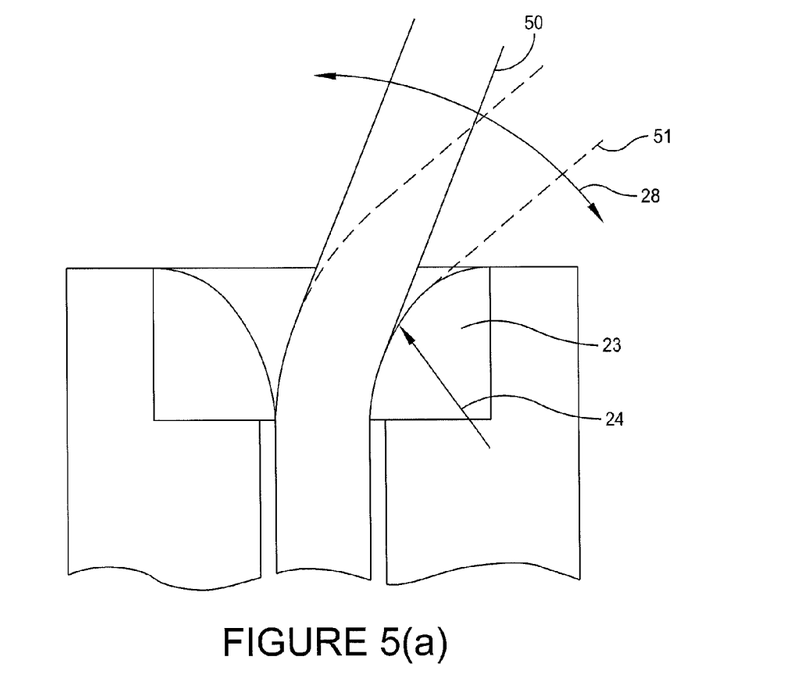
FIG. 5 is a partial cross sectional view of an anchor and ACL prosthesis according to an embodiment of the present invention.
Figure 5B:
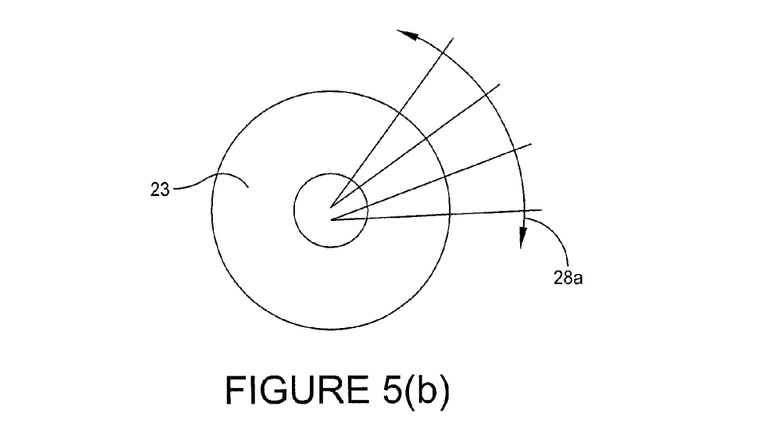

The relationship between the prosthetic ligament and the anchor are illustrated in FIGS. 5(a) and 5(b). The ceramic eyelet 23 is rounded with the radius 24 at the exit of the prosthetic ligament 50. Movement of the ligament through the angle 28 in the cross-sectional view results in the bending of the fibers within the ligament bundle. If the diameter of the fiber 51 is d, and the radius 24 of the rounded eyelet exit is R the maximum strain experienced by the filament bending over the edge is approximately equal to $d/2R$. If the fatigue limit on the strain in the fiber is $\epsilon_{max}$, the radius of the edge should be:

$$R > d/2\epsilon_{max}.$$

With the best expectations of high performance polymeric fibers, the fatigue limit on the strain in the fiber is on the order of 0.015, thus the radius of the eyelet exit edge, R, should be at least 30 times larger than the diameter of the filament, d. The strongest filaments of e.g. highly oriented polyethylene are on the order of 0.015 mm in diameter. For those, the radius should have at the least about 0.5 mm. However, this would leave no capacity to resist any tension. A factor of 2 in the radius, i.e. about 1 mm would allow maximum tension in fatigue to be about one half of its nominal value—a reasonable compromise.

Let the fatigue strain at expected number of cycles in use be $\epsilon_{max}$, the fiber diameter d, and the factor for allowed functional tension k. Then the radius of curvature, R, of the edge of the eyelet should be: $R > (k/2)(d/\epsilon_{max})$. The factor k must be larger than 1, preferably in the range from 2 to 4. The number of fibers needed within a given prosthesis would be determined based on the estimate of the tensile forces it must resist in fatigue.

Existing prosthetic ligaments are either monofilament (used only in veterinary applications) or braided multifilament. Neither type can offer satisfying performance at the anchor exit. For the monofilament fibers the radius of the exit edge required is simply not possible in most situations, i.e. those ligaments will predictably fail in use. Braiding as conventionally done will effectively increase the diameter of the fiber and will also lead to failure. Another serious drawback of braiding is the increased risk of infection—bacteria within a braided suture are not accessible to immune system cells and can thus remain a threat as long as the prosthesis is in the joint. To further increase resistance to infection, fibers, at least some of them, could be prepared with a content of silver, known to have antibacterial properties. All or a portion of the multifilament prosthesis can be held together with a gelatin or other substance which will dissolve within the body. This makes the suture easier to use and to tie, yet allows the filaments to separate in order to achieve improved wear and failure resistance.

FIG. 5(b) shows that the motion of the prosthetic ligament will also have a component 28a leading to sliding at the exit. To minimize potential damage due to wear the surface of the eyelet should be both hard and polished, hence ceramic is a preferred material for the eyelet, either monocrystalline, such as ruby or sapphire, or polycrystalline, such as alumina or zirconia.

In the preferred execution the prosthetic ligament, 45 would be pre-assembled with the femoral anchor 43. After the anchor 43 is screwed into the femur from within the knee joint, the second anchor 44 is screwed into the tibia from proximal to distal, the free end of the ligament is passed through the hole in 44, the ligament is tensioned as needed and a knot is tied and pushed to the distal exit from the anchor 44. The knot can be secured by melting over it a polymer sleeve of melting temperature lower than that of the suture itself. For example if the suture is made from oriented, high modulus, ultra high molecular weight polyethylene with melting temperature of about 150 deg C. the sleeve can be made from a low molecular weight polyethylene melting at about 110 deg C. However, in most applications a simple knot will suffice since the exit of the hole in the anchor is conical and will tend to lock the knot and prevent it from getting loose.

Preferred fiber for construction of the prosthetic ligament of the invention is that of oriented, high modulus, ultra high molecular weight polyethylene, such as DYNEEMA® of DSM, Netherlands, or SPECTRA® from Honeywell, USA. Preferred diameter of the fiber is between 10 and 20 micrometers, preferably about 15 micrometers. Fibers are left free from each other, as in yarn, i.e. no diffusion bonding nor braiding is used in production. The ends may be fused, preferably with an aid of low molecular polyethylene, to facilitate tying of the knots and insertion through the anchors.

Other suitable polymeric fibers are polyethylene teraphtalate (polyester), polyamide (NYLON®), aramid (KEVLAR®), or silk. Resorbable fibers can also be used, e.g. those based on polylactic acid or polyglycolic acid.

The same principles of design of the prosthetic ligament and its anchor can be used in other joints, e.g. for replacement of the so-called round ligament in the hip joint, frequently ruptured by trauma in dogs.

Having disclosed at least one embodiment of the present invention, various adaptations, modifications, additions, and improvements will be readily apparent to those of ordinary skill in the art. Such adaptations, modifications, additions and improvements are considered part of the invention which is only limited by the several claims attached hereto.

The invention claimed is:

1. A ligament prosthesis system comprising a ligament prosthesis and an anchor therefor, wherein the anchor is a tubular bone anchor comprising:
   (a) a longitudinal axis extending from a head at a proximal end of the anchor to a tip at a distal end of the anchor;
   (b) a central, axial hole extending through the anchor from the head to the tip;
   (c) a recess located at an exit of the central, axial hole within the head, the recess having a larger diameter than a diameter of the central, axial hole; and
   (d) a separate ceramic eyelet defining a circular opening, the eyelet being positioned in the recess such that the circular opening communicates with the central, axial hole, and wherein the eyelet has a rounded exit edge, the rounded exit edge having a convexity in a longitudinal direction of the anchor to minimize strain and wear on the ligament prosthesis; and
   wherein the ligament prosthesis is configured to pass through the central, axial hole of the anchor and the circular opening of the eyelet and comprises a plurality of polymeric fibers.

2. The system of claim 1, wherein the ceramic eyelet comprises a monocrystalline material.

3. The system of claim 2, wherein the monocrystalline material is ruby, artificial ruby, or sapphire.

4. The system of claim 1, wherein the ceramic eyelet comprises a polycrystalline material.

5. The system of claim 4, wherein the polycrystalline material is alumina or zirconia.

6. The system of claim 1, wherein the bone anchor comprises a body made from titanium or a titanium alloy.

7. The system of claim 1, wherein the bone anchor comprises a body that is threaded.

8. The system of claim 1, wherein the convexity of the rounded edge has a radius of curvature R of at least size $(k/2)(d/\epsilon_{max})$, wherein d is the diameter of a fiber in the plurality of polymeric fibers, $\epsilon$max is the allowed strain in fatigue of the fibers' material, and k is a factor, larger than 1, allowing for suture tension in cyclic use.

9. The system of claim 8, wherein k is 2-4.

10. The system of claim 1, wherein the convexity of the rounded edge has a radius of curvature R; the polymeric fibers have a diameter d; and R is at least 30 times larger than d.

11. The system of claim 10, wherein the ratio of R:d is 100:1.

12. The system of claim 11, wherein R is 1 mm and d is 10 micrometers.

13. The system of claim 1, wherein the plurality of polymeric fibers have diameters in the range of from 5 to 30 micrometers and are not braided with one another and are not bonded to one another between their ends, but are fused to one another at their ends or knotted at their ends.

14. The system of claim 13, wherein the plurality of polymeric fibers have diameters in the range of from 10 to 20 micrometers.

15. The system of claim 1, wherein the plurality of polymeric fibers are formed from a high strength, high modulus polymer.

16. The system of claim 15, wherein the plurality of polymeric fibers comprises oriented ultra-high molecular weight polyethylene, aramide, or polyethylene terapthalate.

17. The system of claim 1, wherein at least one of the plurality of polymeric fibers comprises an antibacterial agent.

18. The system of claim 17, wherein the antibacterial agent is silver.

* * * * *